US012564297B2

(12) United States Patent
Bathan

(10) Patent No.: US 12,564,297 B2
(45) Date of Patent: Mar. 3, 2026

(54) HANDS-FREE TOILET DEVICE

(71) Applicant: Levy Bathan, San Bernardino, CA (US)

(72) Inventor: Levy Bathan, San Bernardino, CA (US)

( * ) Notice: Subject to any disclaimer, the term of this patent is extended or adjusted under 35 U.S.C. 154(b) by 91 days.

(21) Appl. No.: 18/645,923

(22) Filed: Apr. 25, 2024

(65) Prior Publication Data

US 2024/0398182 A1 Dec. 5, 2024

Related U.S. Application Data

(60) Provisional application No. 63/505,174, filed on May 31, 2023.

(51) Int. Cl.
*A47K 13/10* (2006.01)
*A47K 13/30* (2006.01)
*A61L 2/10* (2006.01)

(52) U.S. Cl.
CPC ............ *A47K 13/10* (2013.01); *A47K 13/302* (2013.01); *A61L 2/10* (2013.01); *A61L 2202/11* (2013.01)

(58) Field of Classification Search
CPC .............................. A47K 13/10; A47K 13/302
USPC ........................................................ 4/246.1
See application file for complete search history.

(56) References Cited

U.S. PATENT DOCUMENTS 1,585,557 A * 5/1926 Miller ....................... E03D 5/08
4/249
2,636,185 A * 4/1953 Boston ................... A47K 13/10
4/246.1

| 4,756,031 | A | | 7/1988 | Barrett | |
|---|---|---|---|---|---|
| 5,056,165 | A | * | 10/1991 | Wescott, Sr. | ........... A47K 13/10 |
| | | | | | 4/246.1 |
| 5,339,468 | A | * | 8/1994 | Lin | ........................ A47K 13/10 |
| | | | | | 4/246.5 |
| 5,444,877 | A | | 8/1995 | Kumarasurier | |
| 7,832,026 | B1 | * | 11/2010 | Bryant | ................... A47K 13/10 |
| | | | | | 4/246.1 |
| 7,975,322 | B1 | * | 7/2011 | Heller | ...................... E03D 5/08 |
| | | | | | 4/411 |
| 8,020,221 | B2 | * | 9/2011 | Borochov | .............. A47K 13/10 |
| | | | | | 4/408 |
| 8,266,730 | B2 | | 9/2012 | Ricca | |
| 8,695,125 | B2 | | 4/2014 | Funari | |
| 2008/0271231 | A1 | | 11/2008 | Stauber | |
| 2015/0167280 | A1 | | 6/2015 | Le | |

* cited by examiner

*Primary Examiner* — Huyen D Le
(74) *Attorney, Agent, or Firm* — Brennan, Manna & Diamond, LLC

(57) ABSTRACT

The device comprises a toilet seat and a toilet seat cover that are both initially in an "up" position. A user can lower the toilet seat by stepping on a foot lever, which is part of a pedal mechanism including a foot lever, lever support, gas spring, extension spring, and chain for tension adjustment. The pedal mechanism facilitates the controlled movement of the toilet seat to a "down" position around the toilet bowl. Additionally, a flush treadle allows for the toilet flushing process by stepping on the same, which in turn pulls a metal cord connected to the toilet flapper, causing the toilet to flush. The device may also be comprised of at least one UV light in the toilet seat cover for sanitizing the toilet seat, activated when the seat is raised, with a power supply regulated by a time delay relay for automatic shutoff.

19 Claims, 9 Drawing Sheets

HANDS-FREE TOILET DEVICE

CROSS-REFERENCE TO RELATED APPLICATION

The present application claims priority to, and the benefit of, U.S. Provisional Application No. 63/505,174, which was filed on May 31, 2023, and is incorporated herein by reference in its entirety.

FIELD OF THE INVENTION

The present invention relates generally to the field of toilets. More specifically, the present invention relates to a hands-free toilet device comprised of a pedal-operated mechanism for raising and lowering the seat, alongside a foot-operated flush mechanism for enhanced hygiene and convenience. The device is also comprised of UV light sanitation for the toilet seat, activated automatically when the seat is raised, with a design that prevents slamming and allows for easy re-sanitization. Accordingly, the present disclosure makes specific reference thereto. Nonetheless, it is to be appreciated that aspects of the present invention are also equally applicable to other like applications, devices, and methods of manufacture.

BACKGROUND

Toilets, particularly those in public spaces, have long been a subject of discomfort and concern when it comes to cleanliness and sanitation. This issue is compounded by the inherent messiness and unsanitary conditions often found in these facilities. The act of lowering the toilet seat and flushing, actions that require direct hand contact, inevitably leads to the spread of germs and bacteria. This risk is not just hypothetical but a real concern that affects everyone who uses these facilities.

In an attempt to mitigate these risks, many individuals resort to wiping down the toilet seat before use, a practice that, while prudent, can be both frustrating and inconvenient. The process becomes particularly cumbersome when one considers the hustle and bustle of daily life, where every moment counts and delays can be more than just minor inconveniences. Furthermore, the alternative of using toilet seat covers, though seemingly a practical solution, brings its own set of challenges. These covers can be awkward to handle, especially in the cramped confines of a toilet stall, and their effectiveness is often questionable. Moreover, when individuals are pressed for time, the effort required to properly place a seat cover can feel disproportionately onerous.

Therefore, there exists a long-felt need in the art for an improved toilet. There also exists a long-felt need in the art for a hands-free toilet device. More specifically, there exists a long-felt need in the art for a hands-free toilet device that allows for hands-free toilet operation.

The subject matter disclosed and claimed herein, in one embodiment thereof, comprises a hands-free toilet device. The device is designed for enhanced user convenience and hygiene. The device comprises a toilet seat and a toilet seat cover that are both initially in an "up" position. A user can lower the toilet seat by stepping on a foot lever, which is part of a pedal mechanism including a foot lever, lever support, gas spring, extension spring, and chain for tension adjustment. The pedal mechanism facilitates the controlled movement of the toilet seat to a "down" position around the toilet bowl. Additionally, a flush treadle allows for the toilet flushing process by stepping on the same, which in turn pulls a metal cord connected to the toilet flapper, causing the toilet to flush. The device may also be comprised of at least one UV light in the toilet seat cover for sanitizing the toilet seat, activated when the seat is raised, with a power supply regulated by a time delay relay for automatic shutoff. This system also includes a mechanism where stepping on the flush treadle releases a catch via a wire rope, enabling the toilet seat to return to its upright position without slamming against the cover, with re-sanitization possible using a foot lever.

In this manner, the hands-free toilet device of the present invention accomplishes all the forgoing objectives and provides an improved toilet. More specifically, the device provides a toilet that allows for hands-free toilet operation.

SUMMARY

The following presents a simplified summary to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a hands-free toilet device. The device is comprised of a toilet seat and a toilet seat cover. In the default position, the toilet seat and toilet seat cover and in an "up" position. To move the toilet seat into a "down" position around a toilet bowl, a user can step on a toilet seat foot lever. While stepping on the toilet seat foot lever, a user can optionally grab at least one support handle.

A user can flush the toilet by stepping on at least one flush treadle. The user can optionally grab the support handle while stepping on the flush treadle. Once the user steps on the flush treadle, the flush treadle pushes a flush bar upward. The upward movement of the flush bar pulls the toilet flapper up, opening the flush valve of the toilet and causing the water to flush inside the toilet bowl. Once a user steps on the flush treadle, the wire rope pulls the plunger (which is preferably an L-shaped bolt) of the spring latch, which releases the spring latch catch, causing a gas spring to extend which raises the toilet seat upward. The extension spring and chain prevent the toilet seat from slamming against the toilet seat cover once this occurs. Once the user removes their foot from the flush treadle, the flush bar lowers down via gravity and the spring latch, wherein said movement is further slowed by the coil spring which is connected under the flush treadle to the treadle stand.

In another embodiment, the toilet seat cover is comprised of at least one ultraviolet (UV) light. When the toilet seat raises upward, the toilet seat's bottom edge pushes at least one switch down and holds the switch while in an upright position. The switch connects a power supply from the alternating current (AC) to the direct current (DC) power converter to the UV lights and to a time delay relay. Once the toilet seat is up, the UV lights turn on to sanitize the toilet seat. The time delay relay turns off the UV lights automatically after the allotted time. To re-sanitize the toilet seat, the user can tap the toilet seat foot lever lightly to turn on the UV lights.

Accordingly, the hands-free toilet device of the present invention is particularly advantageous as it provides an improved toilet. More specifically, the device provides a toilet that allows for hands-free toilet operation. In this manner, the hands-free toilet device overcomes the limitations of existing toilets known in the art.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION

Figure 1:
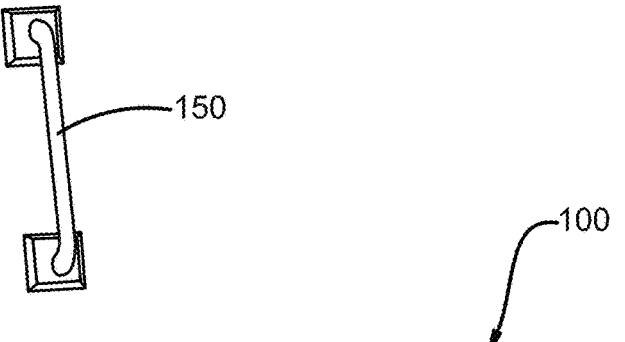
FIG. 1 illustrates a perspective view of one potential embodiment of a hands-free toilet device of the present invention in accordance with the disclosed architecture.
Figure 1:
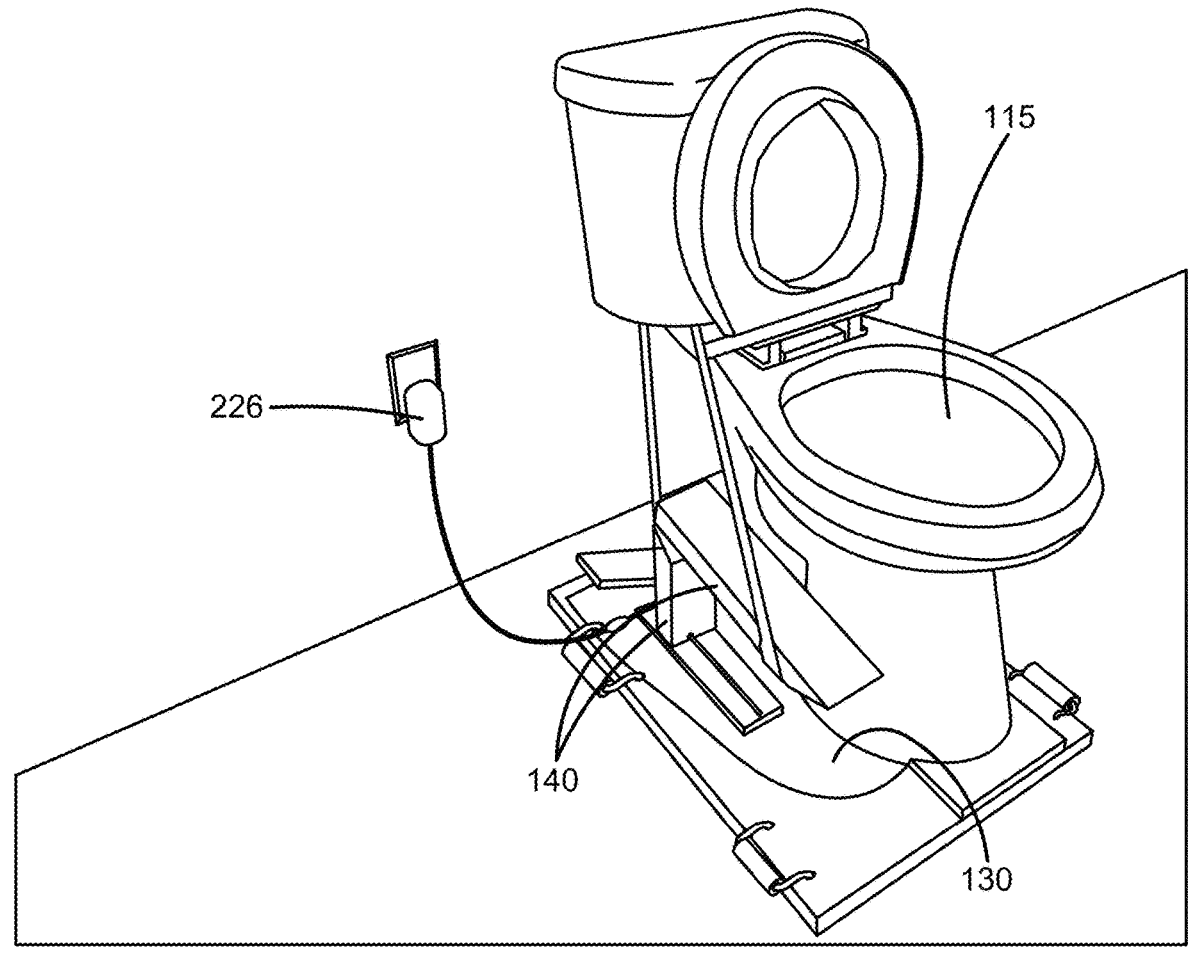

The innovation is now described with reference to the drawings, wherein like reference numerals are used to refer to like elements throughout. In the following description, for purposes of explanation, numerous specific details are set forth to provide a thorough understanding thereof. It may be evident, however, that the innovation can be practiced without these specific details. In other instances, well-known structures and devices are shown in block diagram form to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there exists a long-felt need in the art for an improved toilet. There also exists a long-felt need in the art for a hands-free toilet device. More specifically, there exists a long-felt need in the art for a hands-free toilet device that allows for hands-free toilet operation.

Figure 2:
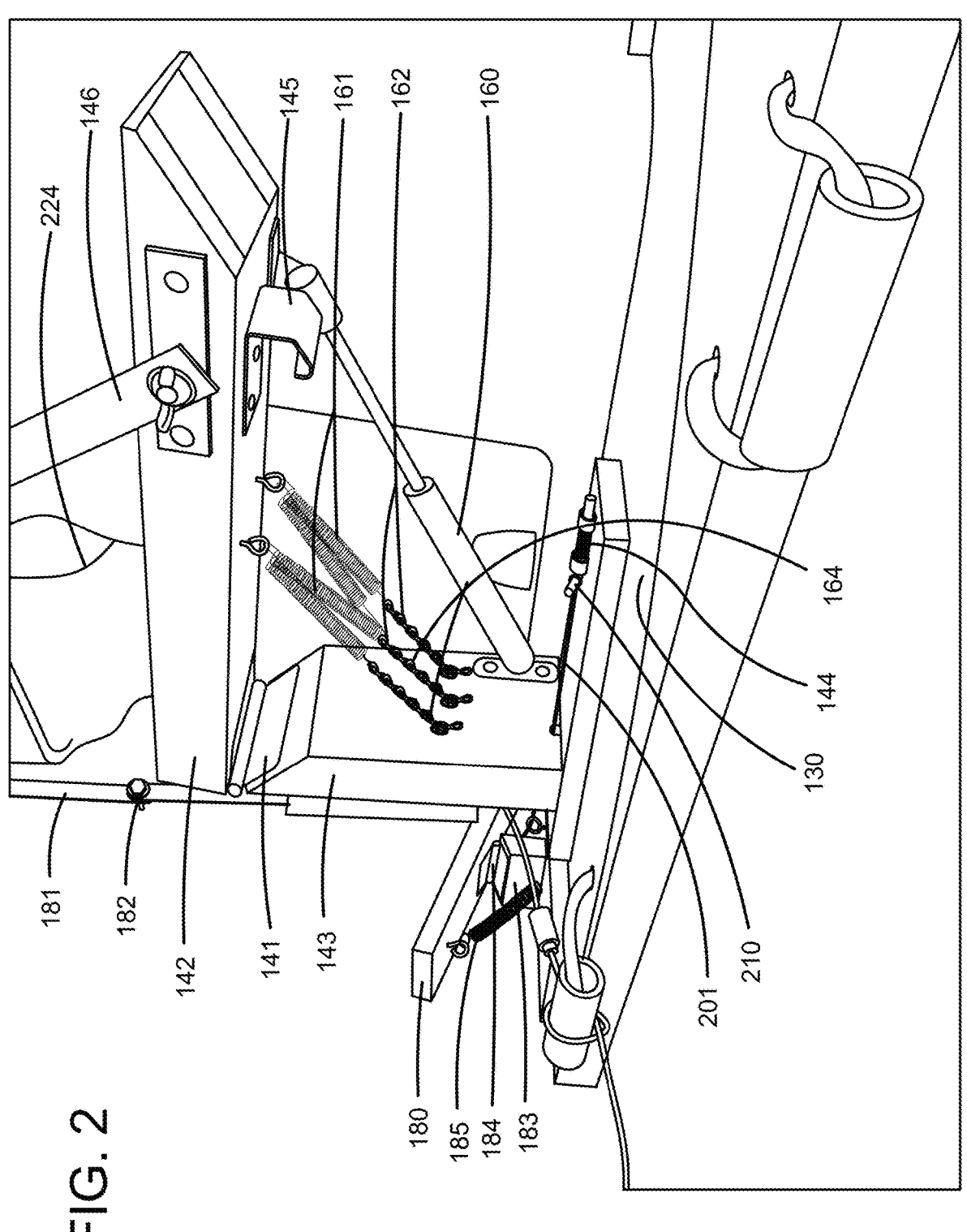
FIG. 2 illustrates an enhanced side perspective view of one potential embodiment of a hands-free toilet device of the present invention in accordance with the disclosed architecture.

Referring initially to the drawings, FIG. 1 illustrates a perspective view of one potential embodiment of a hands-free toilet device 100 of the present invention in accordance with the disclosed architecture. The device is comprised of a toilet seat 110 and a toilet seat cover 120. In the default position, the toilet seat 110 and toilet seat cover 120 and in an "up" position. To move the toilet seat 110 into a "down" position around a toilet bowl 115, a user can step on a toilet seat 110 foot lever 142. While stepping on the toilet seat 110 foot lever 142, a user can optionally grab at least one support handle 150. The toilet seat 110 pedal 140 is comprised of a foot lever 142 and a lever support 143. The top section 147 of the lever support 143 preferably has a 45-degree angle that attaches to a hinge 141 that connects to the toilet seat 110 foot lever 142, as seen in FIG. 2. The toilet seat 110 pedal 140 may also be comprised of at least one gas spring 160 (with a rating but not limited to 25 Newton) and at least one extension spring 161 with at least one chain 162. The tension on the extension spring 161 can be adjusted by adjusting the chain 162 link 164. One end of the gas spring 160 and one end of the chain 162 are (separately) attached to the lever support 143. The other end of the gas spring 160 and the extension spring 161 attaches to the foot lever 142. Stepping on the foot lever 142 compresses the gas spring 160. Once the foot lever 142 is released, the gas spring 160 automatically extends.

Figure 7:
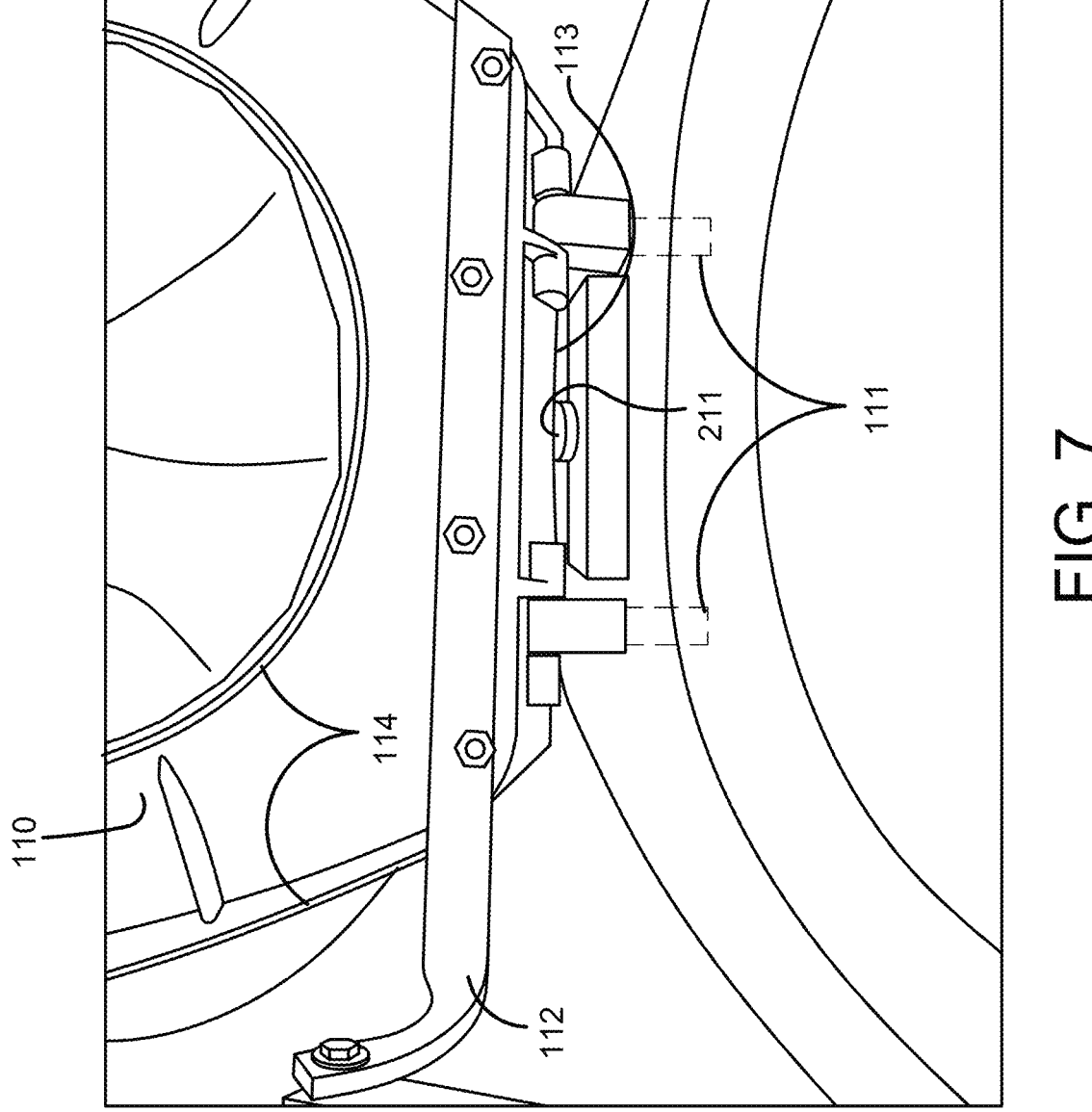
FIG. 7 illustrates an enhanced front view of a toilet seat one potential embodiment of a hands-free toilet device of the present invention in a water tank in accordance with the disclosed architecture.

At least one connecting rod 146 is connected to the foot lever 142 and is positioned before the hinge 141. The connecting rod 146 is connected to a toilet seat 110 bar 112 of the toilet seat 110, as seen in FIG. 7. Once a user steps down on the foot lever 142, the foot lever 142 reaches the base 130 at least one spring latch 144 (positioned under the foot lever 142 and mounted to the base 130) holds at least one spring latch 144 catch 145 (positioned right under the foot lever 142). The spring latch 144 prevents the foot lever 142 from moving upward to allow the toilet seat 110 to sit on the toilet bowl 115.

Figure 5:
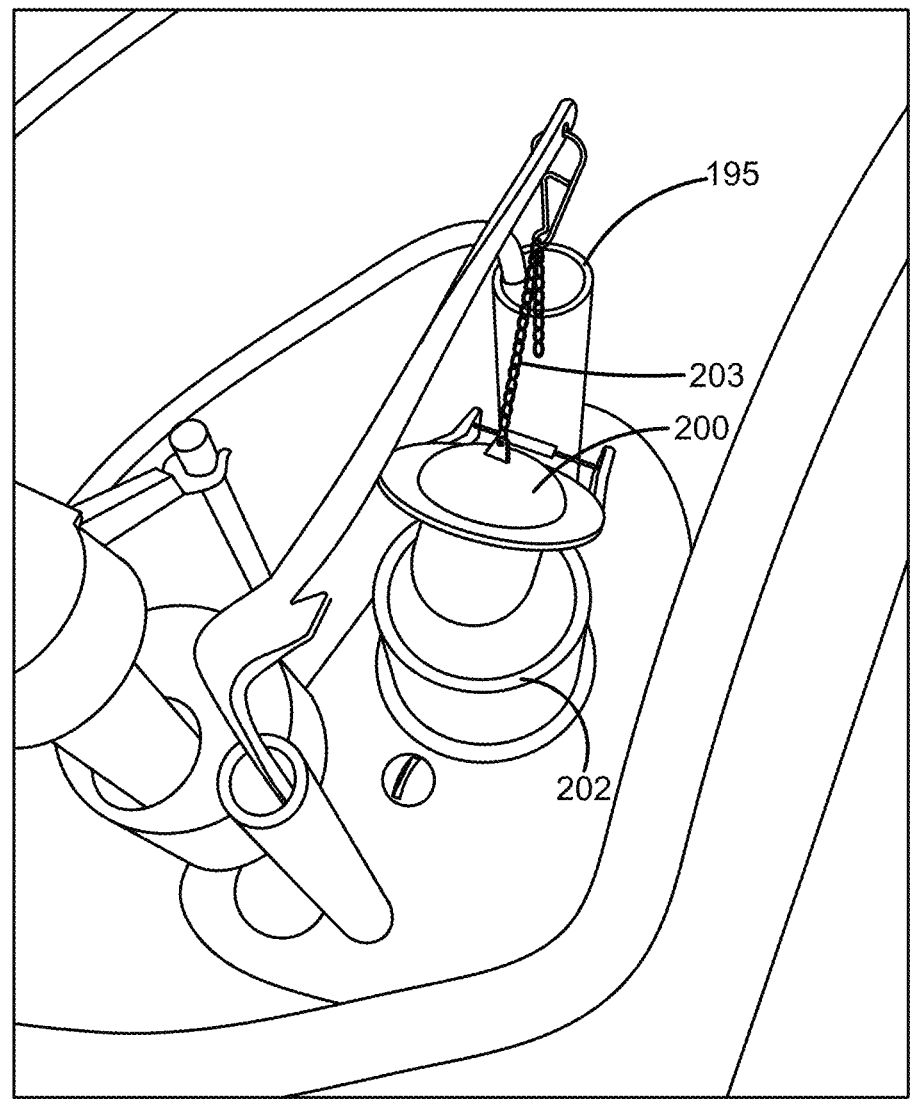
FIG. 5 illustrates a top perspective view of one potential embodiment of a hands-free toilet device of the present invention in a water tank in accordance with the disclosed architecture.
Figure 8:
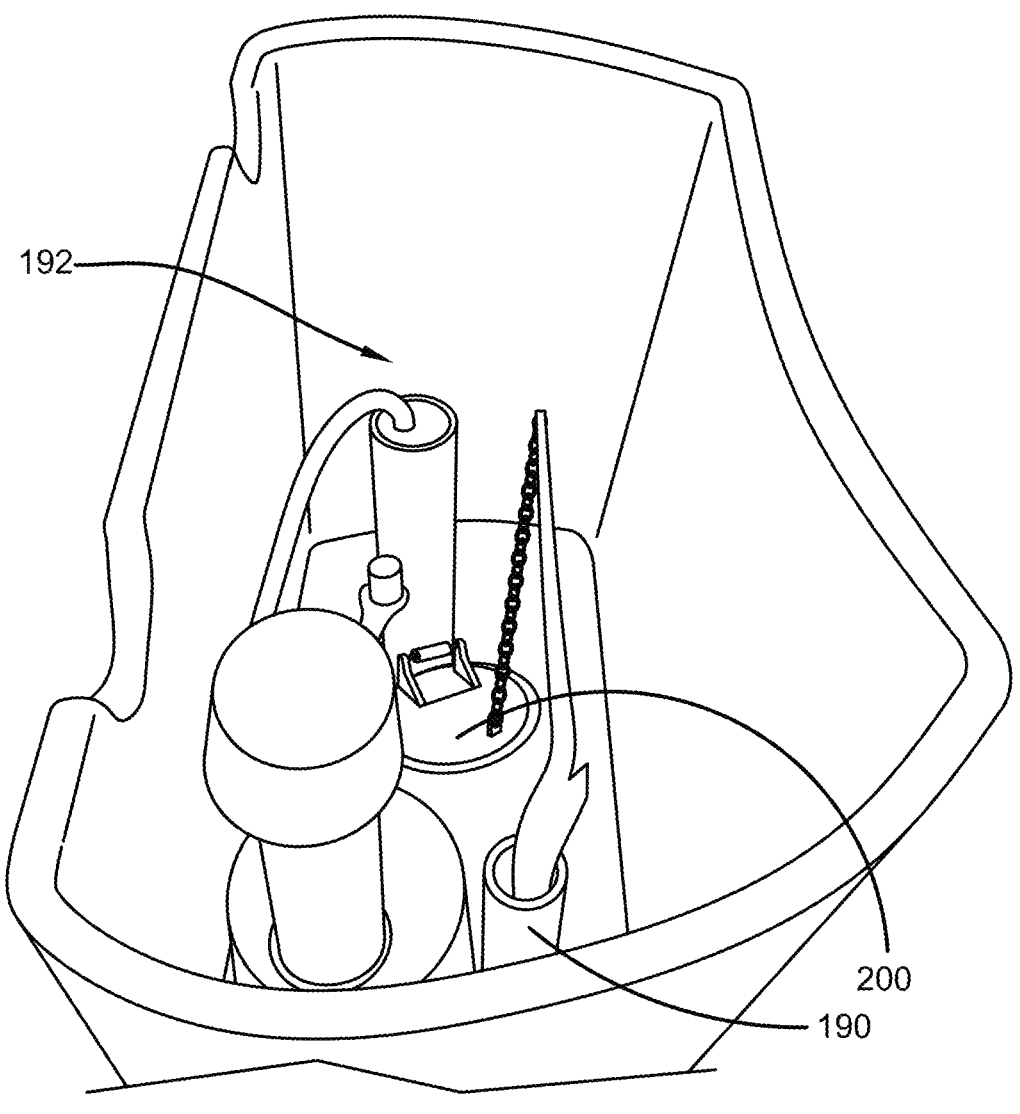
FIG. 8 illustrates a top perspective view of one potential embodiment of a hands-free toilet device of the present invention in a water tank in accordance with the disclosed architecture.

A user can flush the toilet via stepping on at least one flush treadle 180. The user can optionally grab the support handle 150 while stepping on the flush treadle 180. The flush treadle 180 is connected to at least one flush bar 181 that is attached after the axis 184. The flush bar 181 is preferably made from two bars joined together via a joint 182 (such as but not limited to a bolt and nut assembly) wherein the joint 182 serves as a pivot point. The upper portion of the flush bar 181 is positioned inside a tube 190 with lock nut 191 to secure the tube 190, inside of the water tank 192 (as seen in FIG. 8), wherein the tube 190 sits higher than the toilet overflow pipe 195. The flush bar 181 is connected to the toilet flapper 200 of the toilet by a metal cord 203, as seen in FIG. 5. Once the user steps on the flush treadle 180, the flush treadle 180 pushes the flush bar 181 upward. The upward movement of the flush bar 181 pulls the toilet flapper 200 up, opening the flush valve 202 of the toilet and causing the water to flush inside the toilet bowl 115.

The flush treadle 180 may be connected to the spring latch 144 via at least one connector such as but not limited to a wire rope 201. Once a user steps on the flush treadle 180, the wire rope 201 pulls the plunger 210 (which is preferably an L-shaped bolt) of the spring latch 144, which releases the spring latch 144 catch 145, causing the gas spring 160 to extend which raises the toilet seat 110 upward. The extension spring 161 and chain 162 prevents the toilet seat 110 from slamming against the toilet seat cover 120 once this occurs. Once the user removes their foot from the flush treadle 180, the flush bar 181 lowers down via gravity and the spring latch 144, wherein said movement is further slowed by the coil spring 185 which is connected under the flush treadle 180 to the treadle stand 183.

Figure 3:
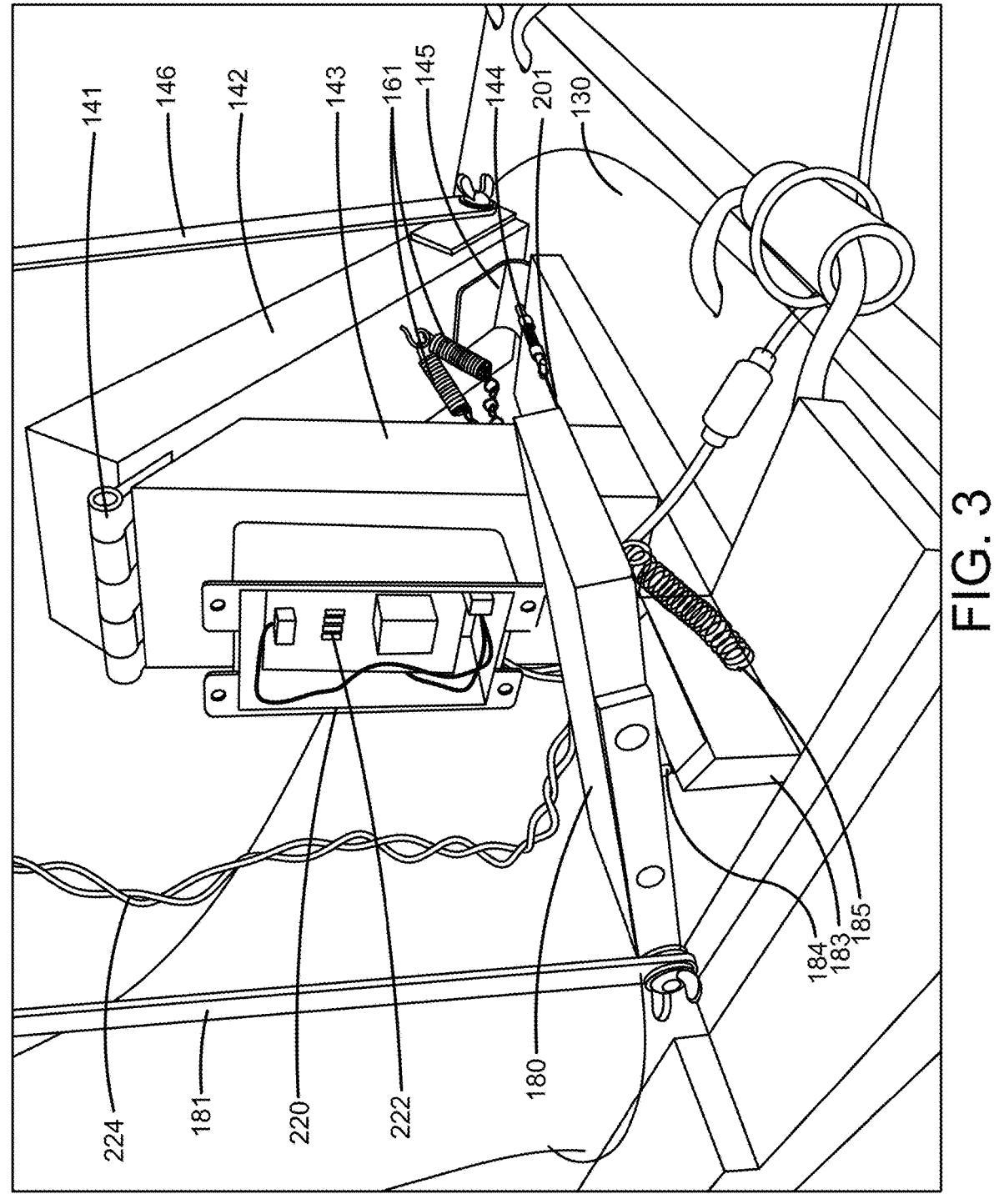
FIG. 3 illustrates an enhanced rear-side perspective view of one potential embodiment of a hands-free toilet device of the present invention in accordance with the disclosed architecture.
Figure 4:
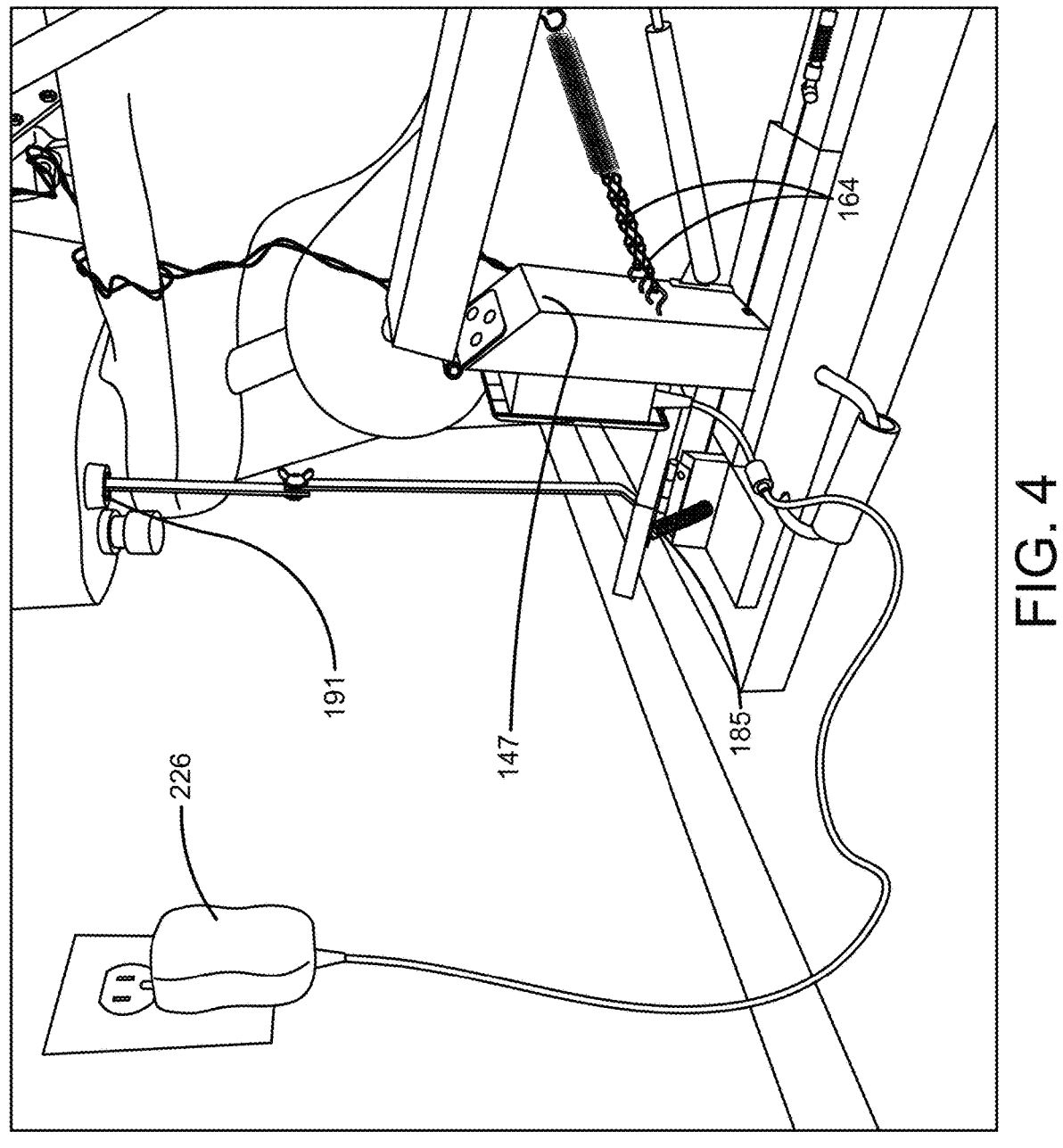
FIG. 4 illustrates an enhanced side perspective view of one potential embodiment of a hands-free toilet device of the present invention in accordance with the disclosed architecture.
Figure 6:
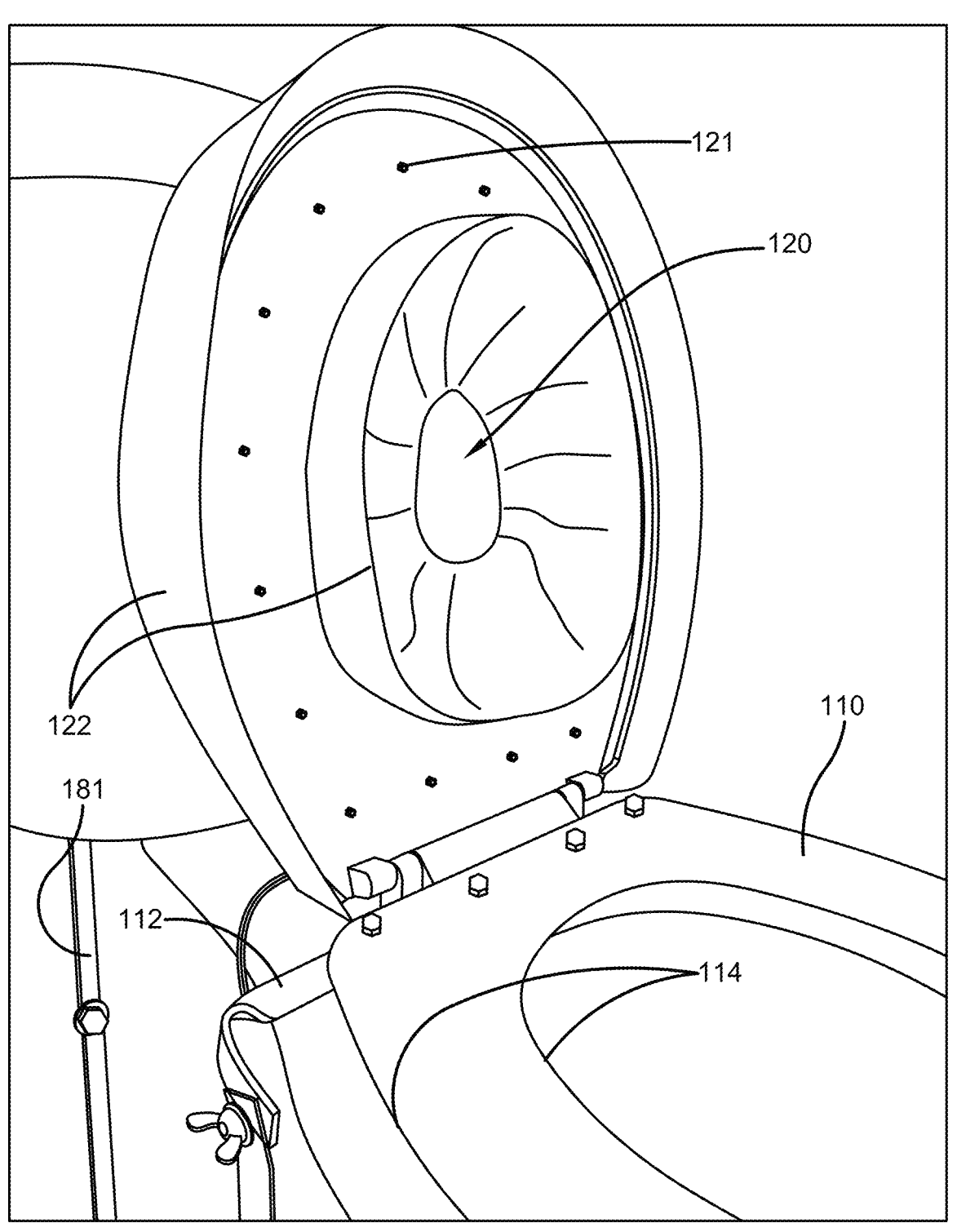
FIG. 6 illustrates a perspective view of a toilet seat one potential embodiment of a hands-free toilet device of the present invention in a water tank in accordance with the disclosed architecture.

In another embodiment, the toilet seat cover 120 is comprised of at least one ultraviolet (UV) light 121 (with a rating but not limited to 40 mJ/cm2), as seen in FIG. 6. The UV light 121 is preferably positioned between at least two toilet seat cover 120 sleeves 122 (with a depth but not limited to 1.5 inches) that is aligned to the interior and exterior edges 114 of the toilet seat 110. The sleeves 122 protect a user from seeing the UV light 121, which can cause eye injury. At least one waterproof spring button switch 211 is installed between the fastener holes 111 of the toilet seat 110. At least one electrical junction box 220 with time delay relay 222 inside (with variable setting), positioned behind the lever support 143, that is connected by wires 224 to UV lights 121 and waterproof spring button switch 211, as seen in FIG. 3.

Figure 9:
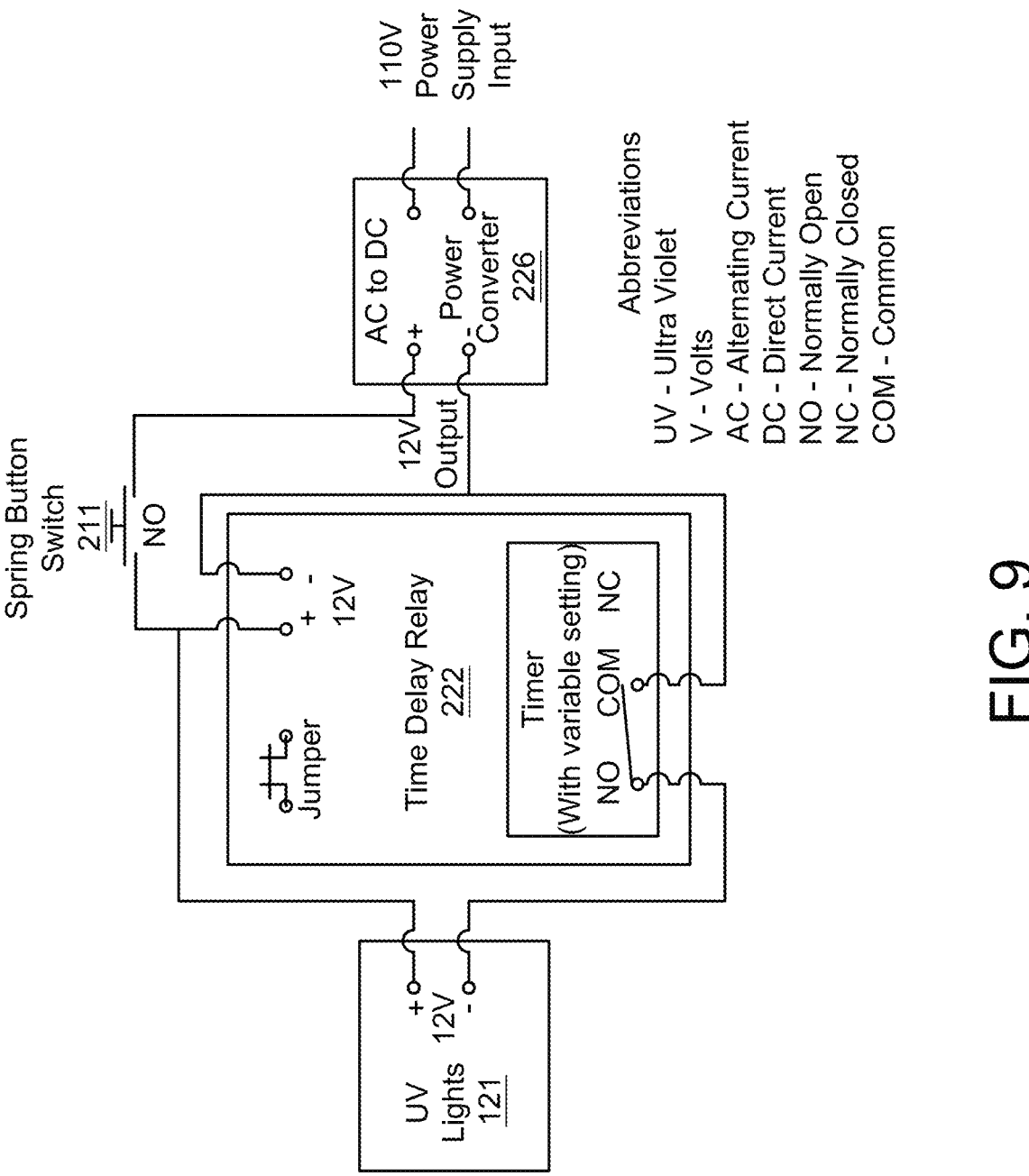
FIG. 9 illustrates a wiring diagram of one potential embodiment of a hands-free toilet device of the present invention in accordance with the disclosed architecture.

When the toilet seat 110 raises upward, the toilet seat 110 bottom edge 113 pushes at least one switch 211 down and holds the switch 211 while in an upright position. The switch 211 connects a power supply from the alternating current (AC) to direct current (DC) power converter 226 to the UV light 121s and to a time delay relay 222. Once the toilet seat 110 is up, the UV lights 121 turn on to sanitize the toilet seat 110. The time delay relay 222 turns off the UV light 121s automatically after the allotted time. To re-sanitize the toilet seat 110, the user can tap the toilet seat 110 foot lever 142 lightly to turn on the UV lights 121. One safety feature of the invention is when the UV lights 121 are on, even with light push on the foot lever 142, the UV lights 121 will turn off immediately to prevent the user's eyes from being exposed to UV lights 121. A wiring diagram of electrical components of the device 100 can be seen in FIG. 9.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "hands-free toilet device" and "device" are interchangeable and refer to the hands-free toilet device 100 of the present invention.

Notwithstanding the forgoing, the hands-free toilet device 100 of the present invention and its various components can be of any suitable size and configuration as is known in the art without affecting the overall concept of the invention, provided that they accomplish the above-stated objectives. One of ordinary skill in the art will appreciate that the size, configuration, and material of the hands-free toilet device 100 as shown in the FIGS. are for illustrative purposes only, and that many other sizes and shapes of the hands-free toilet device 100 are well within the scope of the present disclosure. Although the dimensions of the hands-free toilet device 100 are important design parameters for user convenience, the hands-free toilet device 100 may be of any size, shape, and/or configuration that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A hands-free toilet device comprising:
a foot lever;
a flush treadle;
a connecting rod;
a flush bar;
a hinge that attaches to the foot lever; and
a toilet seat comprised of a toilet seat bar.

2. The hands-free toilet device of claim 1 further comprised of a gas spring that attaches to the foot lever.

3. The hands-free toilet device of claim 1 further comprised of a spring latch catch that attaches to the foot lever.

4. The hands-free toilet device of claim 1, wherein the flush bar attaches to the flush treadle.

5. The hands-free toilet device of claim 1, wherein the connecting bar attaches to the toilet seat bar.

6. A hands-free toilet device comprising:
a foot lever;
a flush treadle;
a connecting rod;
a flush bar;
an electrical junction box;
a time delay relay;
a toilet seat comprised of a toilet seat bar; and
a toilet lid comprised of a UV light, a first sleeve, and a second sleeve.

7. The hands-free toilet device of claim 6, wherein the UV light has a rating of 40 mJ/cm2.

8. The hands-free toilet device of claim 6, wherein the UV light is positioned between the first sleeve and the second sleeve.

9. The hands-free toilet device of claim 6 further comprised of a waterproof spring button switch.

10. The hands-free toilet device of claim 9, wherein depressing the spring button switch turns on the UV light.

11. A hands-free toilet device comprising:
a foot lever;
a spring latch;
a flush treadle;
a connecting rod;
a flush bar;
an electrical junction box;

a time delay relay;

a toilet seat comprised of a toilet seat bar;

a toilet lid comprised of a UV light, a first sleeve, and a second sleeve; and a power converter.

12. The hands-free toilet device of claim 11, wherein the power converter is comprised of an AC to DC power converter.

13. The hands-free toilet device of claim 11 further comprised of a wire rope.

14. The hands-free toilet device of claim 13, wherein the wire rope connects the flush treadle to the spring latch.

15. The hands-free toilet device of claim 11 further comprised of a base.

16. The hands-free toilet device of claim 11 further comprised of a toilet flapper.

17. The hands-free toilet device of claim 11 further comprised of a plunger.

18. The hands-free toilet device of claim 11 further comprised of a flush valve.

19. The hands-free toilet device of claim 11 further comprised of a toilet bowl.

\* \* \* \* \*